United States Patent [19]

Habenstein

[11] 4,372,746
[45] Feb. 8, 1983

[54] AGENT FOR DETECTING PEROXIDATIVELY ACTIVE SUBSTANCES AND THE USE OF A POLYVINYLMETHYLACYLAMIDE IN SUCH AN AGENT

[75] Inventor: Klaus Habenstein, Lahntal, Fed. Rep. of Germany

[73] Assignee: Behringwerke Aktiengesellschaft, Marburg an der Lahn, Fed. Rep. of Germany

[21] Appl. No.: 279,731

[22] Filed: Jul. 2, 1981

[30] Foreign Application Priority Data

Jul. 4, 1980 [DE] Fed. Rep. of Germany ....... 3025372

[51] Int. Cl.³ .................... G01N 33/52; G01N 33/72
[52] U.S. Cl. ....................................... 436/66; 23/932; 252/186.25; 252/408.1; 422/56; 435/28
[58] Field of Search ...................... 23/230 B, 931, 932, 23/913; 422/56, 57; 435/28; 252/408, 186, 186.25

[56] References Cited

U.S. PATENT DOCUMENTS 3,853,471 12/1974 Rittersdorf et al. ............. 422/56 X
4,312,834 1/1982 Vogel et al. ......................... 422/56

FOREIGN PATENT DOCUMENTS 2004062 3/1979 United KingdomC ............. 435/28

Primary Examiner—Arnold Turk
Attorney, Agent, or Firm—Curtis, Morris & Safford

[57] ABSTRACT

Rapid diagnostic agent comprising an absorbent carrier matrix, a chromogen, a hydroperoxide, a detergent, an activator and a compound of the formula I

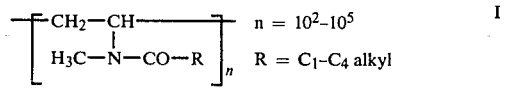

or a copolymer containing such a compound, and, if appropriate, another protective colloid. A diagnostic agent of this type can be used in a method for detecting, in body fluids and excreta, peroxidatively active substances.

8 Claims, No Drawings

AGENT FOR DETECTING PEROXIDATIVELY ACTIVE SUBSTANCES AND THE USE OF A POLYVINYLMETHYLACYLAMIDE IN SUCH AN AGENT

The invention relates to an agent for the determination, in body fluids and excreta, of peroxidatively active substances, which contains a chromogen, a hydroperoxide, a detergent, an activator and a stabilizer.

The detection of peroxidatively active substances, which, in the organism of animals, include hemoglobin and myoglobin, is of considerable importance in the determination of small quantities, invisible to the eye, of blood in body fluids, such as urine or other excreta, such as feces or vomit.

In addition to rapid availability of the result, high sensitivity is a decisive factor for the informative value of a blood test in the case of a microscopic hematuria; these are requirements which can be satisfied by the test papers customary nowadays. However, chromogens which have a high sensitivity of indication and develop very strong colors are required for this purpose. Chromogens which are known to be highly sensitive include benzidines, but the sensitivity of indication of the latter is associated with a stability on storage which in some cases is extremely poor.

In order to stabilize highly sensitive chromogens, attempts have been made to achieve a spatial separation between chromogens and hydroperoxide by successive repeated impregnations. In addition, the reaction has also been carried out using stabilizers and stabilizing solvents. Film-forming protective colloids have also already been used. Polyvinylpyrrolidine has been described as such a colloid in German Offenlegungsschrift No. 2,546,252. However, none of these procedures has hitherto produced a satisfactory improvement. On the other hand, a distinctly stabilizing effect is achieved by the use of microencapsulated hydroperoxides, but this involves the disadvantage of a reduction in sensitivity of indication as well as a non-uniform and blotchy indication.

It has now been found, surprisingly, that a high degree of stabilization of the chromogen on the test paper is achieved by using, as the protective colloid, a polyvinylmethylacylamide of the formula I

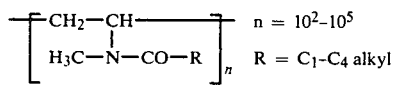

$$\left[\begin{array}{c}CH_2-CH \\ | \\ H_3C-N-CO-R\end{array}\right]_n \quad \begin{array}{l} n = 10^2-10^5 \\ R = C_1-C_4 \text{ alkyl}\end{array} \quad \text{I}$$

Preferred ranges are as follows: $n = 10^3-10^4$; $R = C_1-C_2$ alkyl.

The invention therefore relates to an agent for the determination, in body fluids and excreta, of peroxidatively active substances, which contains a chromogen, a hydroperoxide, a detergent, an activator and a stabilizer and wherein the stabilizer comprises a compound of the formula I or contains such a compound.

The stabilizer can contain up to 40%, preferably up to 30%, of another protective colloid. Furthermore, the stabilizer can be a copolymer having a content of at least 60%, preferably at least 70%, of a compound of the formula I.

Examples of suitable hydroperoxides are the hydroperoxides of cumene, tetralin, decalin or pinane. Stabilizers of the EDTA type protect the hydroperoxide by capturing traces of heavy metals. Instead of the benzidine derivatives, it is possible to use, inter alia, guaiacol or heterocyclic azines.

Substances of the type of sodium dodecylsulfate can be used as the detergents.

In principle, the material of the water-absorbing test area is not critical. Fiber fleeces composed of cellulose or plastic are generally used. However, non-fibrous systems are also known, in which the chemicals are incorporated in a water-absorbing film.

If the agent contains a buffer, examples of suitable buffers are citrates, phosphates or phthalates, which produce a pH value of 4–7, preferably 5–6, after the test area has been moistened.

In order to prove the superiority of the agent according to the invention over agents of the state of the art, test strips were prepared using one of the stabilizers suggested and using, in each case, a particular stabilizer from a selection of known stabilizers, and their stability on storage was compared. The decrease with time in the sensitivity of indication of test strips which had been stored at 50° C. was used as a criterion of the protective action of the stabilizers.

It was found that the sensitivity of indication of the test strips according to the invention decreased to a considerably smaller extent than that of test strips containing known stabilizers.

The invention is illustrated in greater detail by the following example.

EXAMPLE

Preparation of the test papers

Pieces of indicator base paper having an area of about 100 cm² and a weight per unit area of about 150 g/m² are impregnated successively with the following solutions and are, in each case, subjected to an intermediate drying (using a circulating air drying cabinet at 80° C.):

1. The impregnating solution contains 40 mg of otolidine hydrochloride and 20 mg of 4-azafluorene in 10 ml of methanol;

2. The impregnating solution contains 20 ml of sodium dodecylsulfate, 10 mg of EDTA, 7.5 mg of tartrazine and 300 mg of a compound of the formula I in which $n=1,400$ and $R=CH_3$, dissolved in 10 ml of a 0.24 molar citric acid buffer, pH 5.5;

3. The impregnating solution contains 250 mg of cumene hydroperoxide in 10 ml of Frigen ®.

The finished papers are stored in cans containing a drying agent.

A test strip of similar stability is obtained by using a product which has an average molecular weight of $10^6$. The viscosity of the 2nd impregnating solution is then higher, however. The addition of water-repellant copolymers gives a polyvinylmethylacylamide which enables the test paper produced to be modified so that it can be graded in an improved manner.

A good stabilizing effect is also achieved using a mixture composed of about 70% of the above product and about 30% of another film-former, for example a starch derivative. It can be seen from this that a pronounced stabilizing effect can also be achieved by adding the protective colloid according to the invention to film-formers which, in themselves, are unsuitable.

I claim:

1. A rapid diagnostic agent for detecting, in body fluids and excreta, peroxidatively active substances, which comprises an absorbent carrier matrix containing a chromogen, a hydroperoxide, a detergent, an activator and a stabilizer, wherein the stabilizer comprises a compound of the formula I

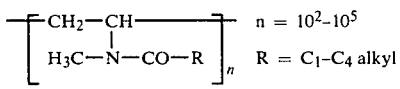

or contains such a compound.

2. A rapid diagnostic agent as claimed in claim 1, wherein n is $10^3$–$10^4$.

3. A rapid diagnostic agent as claimed in claim 1, wherein R is $C_1$–$C_2$ alkyl.

4. A rapid diagnostic agent as claimed in claim 1, wherein the stabilizer contains a compound of the formula I and up to 40% of another protective colloid.

5. A rapid diagnostic agent as claimed in claim 1, wherein the stabilizer contains a compound of the formula I and up to 30% of another protective colloid.

6. A rapid diagnostic agent as claimed in claim 1, wherein the stabilizer is a copolymer containing at least 60% of a compound of the formula I.

7. A rapid diagnostic agent as claimed in claim 1, wherein the stabilizer is a copolymer containing at least 70% of a compound of the formula I.

8. A method for detecting, in body fluids and excreta, peroxidatively active substances, which comprises bringing a diagnostic agent as claimed in claim 1 into contact with the body fluid or excreta to be tested and observing any resultant color change.

* * * * *